(12) United States Patent
Nance

(10) Patent No.: US 11,931,450 B2
(45) Date of Patent: Mar. 19, 2024

(54) HAIR OIL

(71) Applicant: Sa'Rai Nance, Milwaukee, WI (US)

(72) Inventor: Sa'Rai Nance, Milwaukee, WI (US)

( * ) Notice: Subject to any disclaimer, the term of this patent is extended or adjusted under 35 U.S.C. 154(b) by 14 days.

(21) Appl. No.: 17/868,419

(22) Filed: Jul. 19, 2022

(65) Prior Publication Data

US 2023/0036773 A1  Feb. 2, 2023

Related U.S. Application Data

(60) Provisional application No. 63/223,802, filed on Jul. 20, 2021.

(51) Int. Cl.
| | | |
|---|---|---|
| *A61K 8/92* | (2006.01) | |
| *A61K 8/65* | (2006.01) | |
| *A61K 8/9789* | (2017.01) | |
| *A61K 8/9794* | (2017.01) | |
| *A61Q 5/12* | (2006.01) | |

(52) U.S. Cl.
CPC ............ *A61K 8/922* (2013.01); *A61K 8/65* (2013.01); *A61K 8/92* (2013.01); *A61K 8/9789* (2017.08); *A61K 8/9794* (2017.08); *A61Q 5/12* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 6,372,234 B1 | 4/2002 | Deckers et al. | |
| 7,025,955 B2 | 4/2006 | Siddiqui et al. | |
| 8,025,908 B2 | 9/2011 | Anderson | |
| 8,221,731 B2 | 7/2012 | Gutmann et al. | |
| 8,586,105 B2 | 11/2013 | Anderson | |
| 9,669,241 B2 | 6/2017 | Wycoff et al. | |
| 2013/0236413 A1 | 9/2013 | Sargent | |
| 2015/0216768 A1 | 8/2015 | May et al. | |
| 2020/0188351 A1 | 6/2020 | Coto | |
| 2023/0062111 A1* | 3/2023 | Sakata | C07K 5/06026 |

FOREIGN PATENT DOCUMENTS

| | | |
|---|---|---|
| CA | 2571312 | 10/2011 |
| CN | 107308036 | 11/2017 |
| CN | 107418790 | 12/2017 |
| CN | 107737079 | 2/2018 |
| CN | 110664663 | 1/2020 |
| WO | WO2009/148825 | 12/2009 |
| WO | 2020/065541 | 4/2020 |

* cited by examiner

*Primary Examiner* — Nannette Holloman
(74) *Attorney, Agent, or Firm* — RYAN KROMHOLZ & MANION, S.C.

(57) ABSTRACT

A natural hair oil treatment product and methods of producing the hair oil and using the oil. The hair oil includes multiple vegetable oils and natural products that are combined in a multi-step process, with the products providing therapy and/or treatment for the hair and scalp.

16 Claims, No Drawings

HAIR OIL

RELATED APPLICATIONS

This application claims priority to provisional U.S. Pat. No. 63/223,002, filed on 20 Jul. 2021.

BACKGROUND OF THE INVENTION

The present invention relates to hair products and more particularly to organic hair treatments.

There is desire in modern hair products to provide products that have natural and organic ingredients as opposed to synthetic or inorganic materials. However, there is often an efficacy trade-off with natural ingredients compared to synthetic ingredients.

Hair products must also accommodate varying types of hair, and particularly thick, textured hair that may be subject to kinking and knotting. Similarly, hair products are preferred that can treat: one's hair without harsh chemicals that may damage the hair follicles.

There is a need for hair products that will address these issues.

SUMMARY OF THE INVENTION

The present invention is an organic hair treatment product. More specifically, the present invention is an organic hair oil for treating a person's hair.

The hair oil of the present invention generally comprises a three part formulation. The formulation comprises various natural oils and various natural ingredients.

The natural oils of the present invention may include fruit and vegetable oils, including castor oil, olive oil, grapeseed oil, avocado oil, coconut oil, macadamia oil, walnut oil, sunflower oil, sesame oil, jojoba oil, and sweet almond oil. The natural oils of the present invention may also include natural aromatic oils, including lavender oil, Eucalyptus oil, rosemary oil, peppermint oil, cedarwood oil, orange oil, argan oil, thyme oil, safflower oil and tea tree oil.

The natural ingredients of the present invention may include black tea, saw palmetto, garlic powder, onion powder, neem powder, rose petal powder, amla powder, bhringraj powder, henna powder, mutamba powder, shikaki powder, and lemon grass.

The natural ingredients of the present invention may further include liquid collagen biotin, and methylsulfonylmethane.

The present invention is also directed towards methods for producing a hair oil. More specifically, the present invention is directed towards methods of producing a natural hair oil formulation. The methods comprises the first step of combining various ingredients and baking the combination, followed by steps of heating and boiling other ingredients together.

Yet another aspect of the present invention is directed towards methods of treating hair using the formulations of the present invention. The present invention provides a hair oil that can help color hair and also treat graying hair.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the claims.

The hair oil of the present invention is a natural hair product that includes various ingredients having therapeutic properties for the treatment of the hair. The hair oil is produced in a series of steps, with different ingredients added at each of the steps. Generally speaking, the steps include a first step of layering ingredients and baking the ingredients, followed by individual steps of combining ingredients and boiling the ingredients to form a solution. The process further includes a step of storing individually the composition of the first from the compositions of the individual stops.

when referring to steps such as simmering and boiling, it is understood that these terms have their ordinary meaning as used in cooking processes, and references to high, medium, and low heats also have their ordinary meaning for cooking purposes.

Part 1

Part 1 of the formulation is designed to provide therapeutic qualities for the person's hair, such as moisturizing the hair, strengthening the hair, and potentially promoting hair growth. Part 1 is generally a combination of castor oil, black tea, cayenne pepper, collagen, biotin, methylsulfonylmethane (MSM), saw palmetto, garlic powder, and onion powder. Each of these ingredients contributes to the therapeutic properties of the invention.

For example, castor oil is known to be a moisturizer for hair. Black tea, which comes from the leaves of the *Camellia sinesnis* plant, is believed to increase hair growth, enhance hair color, and boost hair sheen. Collagen increases hair building proteins, potentially resulting in longer thicker hair. Collagen can potentially reduce the appearance of grey hair. Biotin, which is a B vitamin complex, also sometimes referred to as vitamin H, may be used to combat hair loss, as can saw palmetto. MSM may promote hair growth. Similarly, cayenne pepper, onion powder, arid garlic powder promote hair growth and may also be used to promote hair strength, as well.

Part 1 is assembled in layers, with the first layer comprising castor oil. The layers are as follows:
1. Castor oil
2. Black tea
3. Cayenne Pepper
4. Garlic powder
5. Onion powder
6. Collagen
7. Biotin
8. MSM
9. Saw palmetto Preferably, castor oil comprises the largest portion or component of part 1, at least 50% or more, and preferably between 55%-65%, and roost preferably approximately 60%. In one solution, 16 ounces (oz.) of castor oil is added to a container, followed by approximately 75 grams of black tea. The black tea could be bulk tea or could be from tea bags, e.g. Earl Grey tea bags. The spices, cayenne pepper (1.5 oz.), 6 Tablespoons (T) garlic powder, and 3 T onion powder are added in order to the container. Liquid collagen (~0.5 teaspoon) is added, followed by the addition of blot in. Biotin is sold in a capsule form or as a liquid. Either is acceptable for the present invention. For example, 25 capsules (10,000 mg) of biotin may be added, or 4 drops of liquid biotin may be added. MSM is subsequently added, e.g. 50 tablets of MSM (1000 mg) which have been crushed into a powder. The saw palmetto is added as the final layer.

The saw palmetto can be purchased in capsule form or can come in a bulk form. Approximately 2 oz. is added to the solution.

Once the ingredients are layered, the solution will then be baked in an oven at 200° F. (93.3° C.) for approximately 5 hours. The solution will then be allowed to test for an additional 5 hours, with the castor oil solution strained from the black tea. Part I will then be set aside for future assembly.

Part 2

Part 2 of the hair oil formulation generally comprises vegetable oils, including olive oil, grape oil, avocado oil, coconut oil, and macadamia oil. Vegetable oils are beneficial for hair, as they contain carbohydrates and essential fats and nutrients that can repair porous and damaged hair.

Part 2 also includes various powders that further provide benefits to hair. For example, neem powder, rose petal powder, and amla powder, preferably comprise part 2, which help strengthen the scalp and hair follicles and help prevent dandruff. Part 2 also comprises Bhringhaj powder, Brahmi powder and mutamba powder, which strengthen hair and can be used to treat split ends. Henna powder may also comprise part 2, which can help in treating grey hair.

As noted above, part 2 generally comprises at least vegetable oils of part 2, and the remaining amount of part 2 comprising various powders. Preferably at least 95% of part 2 comprises vegetable oils, with the remaining amount of part comprising various powders, and most preferably comprises over 80% vegetable oils. In one preferred embodiment, part 2 comprises more than one of the noted vegetable oils, preferably comprising at least 40% olive and preferably at least about 50% olive oil.

Part 2 of the formulation is assembled by combining a first portion of a vegetable oil with a first portion of a powder in a container. Preferably the oil and the powder are combine in a 2:1 ratio. For example, 2 cups of oil could be combined with 1 cup of powder. The combination is then heated ever a low heat so that the combination begins to simmer. Once the initial combination has simmered for approximately 20 minutes, the remaining amounts of the vegetable oils and the powders can be added, and the solution will be brought to a boil, preferably at a low to medium heat. Once a boil is achieved, heat can be removed from the solution and the solution will be allowed to rest for approximately 20 minutes.

A further example of preparing part 2 of the hair oil comprises the step of combining 2 cups (16 oz.) of extra virgin olive oil with 1 cup (8 oz.) of Mutamba powder. The combination is simmered over low heat for approximately 20 minutes. After that, further ingredients are added, comprising approximately 6.5-7 cups (52-58 oz.) of additional vegetable oils and approximately 3-5 oz. of additional powders. The added ingredients are then incorporated to form a solution, with the solution brought to a boil, preferably at a low to medium heat. The solution is removed from the heat and allowed to rest for 20 minutes.

The additional vegetable* oils are preferably selected from extra virgin olive oil, grape seed oil, avocado oil, coconut. oil, and macadamia oil and combinations of these. For example, the additional oils could be as follows: 3 cups of extra virgin olive oil, 1.5 cups of grapeseed oil, 0.5 cups of avocado oil, 1 oz. of coconut oil, and 0.5 cup macadamia oil.

The additional powders added to the solution are preferably selected from neem powder, rose petal powder, amla powder, Bhringraj powder, Brahmi powder, and henna powder and combinations of these. Each powder preferably would be added in reasonably equal amounts, e.g. 0.5 oz. of each.

Part 3

Part 3 of the hair oil formulation of the present invention is directed towards a combination of vegetable oils and aromatic oils. Part 3 of the hair oil generally is prepared similarly to parts 1 and 2 of the hair oil in that the ingredients are added together and brought to a boil.

Part 3 comprises components and ingredients that are intended to strengthen hair and prevent or minimize split ends, such as sunflower oil, sesame oil, jojoba oil, and sweet almond oil, safflower oils are vegetable oils contemplated for use in part 3. Part 3 includes one or more of these vegetable oils. Part 3 also include ingredients for addressing hair loss and hair growth, such as walnut oil, olive oil, grapeseed oil, thyme oil, and argan oil.

A further benefit of the ingredients in part 2 is the ability to treat the scalp and dandruff. Such ingredients as shikakai powder and tea tree oil are included in part 3.

Part 3 further includes several ingredients that have therapeutic properties for hair, but also provide an appealing aroma for the hair oil. For example aromatic oils may be included in part 3. Such aromatic oils include lavender oil, eucalyptus oil, rosemary oil, peppermint oil, lemongrass oil, cedarwood oil, and orange oil. It is also understood that these aromatic oils have therapeutic qualities for the hair, similar to the ingredients noted above.

In one example of part 3 of the hair oil, a solution comprising about 89-93 oz. is prepared, with the majority of the solution comprising vegetable oils. Preferably 75% or more of part 3 comprises vegetable oils, and more preferably 85% or mere comprises vegetable oils.

Initially, approximately 16 oz. of walnut oil, 16 oz. of sweet almond oil, 24 oz. of sunflower oil, 8 oz. of grapeseed oil, and 4 oz. of Shikakai powder are combined and then heated over a medium heat and brought to a boil. Once brought to a boil, the heat is turned to low, end the remaining ingredients of part 3 are added to the solution. Preferably, this would include approximately 8 oz. of sunflower oil, 1 oz. of jojoba oil, 4 oz. of olive oil, 2 oz. of argan oil, 2 oz. thyme oil, 4 oz. of safflower oil, and 1 oz. of tree oil, as well as the aromatic oils. The preferred aromatic oils, lavender. Eucalyptus, rosemary oil, peppermint oil, lemongrass, cedarwood oil, and orange oil, are added with an eye dropper, preferably 1-10 drops of each oil.

Once all of the ingredients are added, the solution is allowed to cook, e.g. fuse, for approximately 10 minutes and then allowed to cool.

Once cooled, part 2 and part 3 of the solution will be combined and brought to a slow boil and allowed to cook at a low temperature for approximately 5 minutes. After cooking, if any of the powders nave separated out from the oil, separate and remove them from the solution.

Once the part 2/part 3 solution is finally combined, the part 2/part 3 solution will be recombined with the part 1 solution. Preferably, the solutions are combined in a 1:7 ratio of part 1 to part: 2/part 3 and stored in an airtight bottle out of direct sunlight. For example, 0.5 oz. of part 1 could be stored with 3.5 oz. of part 2/part 3 and stored for future use.

It is understood that the values used above are approximate. The values may be modified somewhat and fail within the scope of the present invention.

Use

The prepared hair oil can be applied to a person's hair. The person's hair will be washed and then towel dried. Afterwards, the hair oil will be applied, with the hair oil remaining on the hair for predetermined amount of tine and then washed out. Preferably the hair oil is left in for 30 minutes or longer, depending on the particular hair being treated.

The present invention provides a unique combination of therapeutic ingredients for the treatment of hair. While many of the above ingredients have been contemplated for the use of hair treatment, they have not been combined or processed as described, herein. Likewise, the balance between the liquid oils used in the present invention with the powder ingredients has been balanced between two so as to provide an efficacious hair oil, with the hair oil nor being overpowering. The unique combination provides a more efficacious hair oil and treatment than previous hair oils. For example, the hair oil provides a unique and novel arrangement for treating the graying of hair end is believed, in fact, to slow down the graying process. The hair oil has also the potential to provide other therapeutic, such as strengthening the hair and treating dry scalp, dandruff, and other conditions. Furthermore, it: is believed that the present invention provides an improved hair oil and treatment compared to prior art oils and solutions in that it is derived from natural and organic ingredients.

A study, No. C21-5021.01, was conducted by the Consumer Product Testing Company, Inc. 70 New Dutch Lane, Fairfield, N.J. 07004. The study was conducted between Sep. 27, 2021 and Nov. 12, 2021 to determine whether a formulation according to the present invention would induce primary or cumulative irritation and/or allergic contact sensitization.

The test included fifty-six qualified subjects, both male and female, ranging in age from 20 years to 73 years. Fifty of the patients completed the clinical trial. with the remaining subjects discontinuing the study for various reasons, none of which were related to the application of the formulation.

The testing was carried out by placing approximately 0.2 mL of the test formulation on the upper back between the scapulae. The amount was sufficient to cover the contact surface and was applied to a 1 in$^2$ absorbent pad portion of a clear, adhesive dressing and allowed to volatize for approximately 10 minutes. The pad was then applied to the treatment area site to form a semi-occlusive patch.

Induction patches were applied three (3) times per week (e.g. Monday, Wednesday, and Friday) for a total of none (9) applications, with rest days for the remainder of the week. The site was marked to ensure the continuity of patch application.

At least 10 days following the final induction patch, a Challenge patch was applied to a virgin test site adjacent to the final patch, with application carried out as with the testing for the original applications. The test areas were evaluated as follows:

| Evaluation Criteria (Erythmea and additional Dermal Sequelae | |
| --- | --- |
| 0 = No visible skin reactions | E = Edema |
| 0.5 = Bareley perceptible | D = Dryness |
| 1 = Mild | S = Staining |
| 2 = Moderate | P = Papules |
| 3 = Marked | V = Vesicles |
| 4 = Severe | B = Bullae |
| | U = Ulceration |
| | Sp = Spreading |

Erythema was scored numerically according to this key. If present, additional Dermal Sequelae were indicated by the appropriate letter code and a numerical value for severity.

One of the subjects reported contact dermatitis on the upper and lower back, cut not on the treated site. She was treated by a Board Certified Dermatologist, who treated the symptoms and followed-up to determine the subject was asymptomatic.

The remaining subjects ail were numerically scored at zero (0) throughout the testing, indicating that the formulation of the present invention does nor pose reactivity issues when used as a hair treatment.

The foregoing is considered as illustrative only of the principles of the invention. Furthermore, since numerous modifications and changes will readily occur to those skilled in the art, it is not desired to limit the invention to the exact construction end operation shown and described. while the preferred embodiment has been described, the details may be changed without departing from the invention, which is defined by the claims.

I claim:

1. A therapeutic hair oil product, comprising:
a first part comprising at least 50% castor oil, collagen, and at least one component selected from the group consisting of: black tea, cayenne pepper, garlic powder, and onion powder and combinations thereof;
a second part comprising at least 50% of a vegetable oil; and
a third part comprising an aromatic oil,
wherein said hair oil product enhances the hair by treating graying of the hair and moisturizing and strengthening the hair, wherein said enhancement of the hair can lead to the promotion of hair growth.

2. The hair oil according to claim 1, where said first part further comprises at least one further component selected from the group consisting of: biotin, methylsulfonylmethane (MSM) and saw palmetto and combinations thereof.

3. The hair oil product according to claim 1, wherein said second part further comprises at least one further component selected from the group consisting of: neem powder, rose pedal powder, and amla powder and combinations thereof.

4. The hair oil product according to claim 3, wherein said second part further comprises at least one further component selected from the group consisting of: Bhringhaj powder, Brahmi powder, mutamba powder, and henna powder and combinations thereof.

5. The hair oil product according to claim 1, wherein said third part further comprises a second vegetable oil.

6. The hair oil product according to claim 5, said second vegetable oil is selected from the group consisting of: sunflower oil, sesame oil, jojoba oil, and sweet almond oil, safflower oils, walnut oil, olive oil, grapeseed oil, thyme oil, and argan oil and combinations thereof.

7. The hair oil product according to claim 6, wherein said aromatic oil is selected from the group consisting of: lavender oil, eucalyptus oil, rosemary oil, peppermint oil, lemongrass oil, cedarwood oil, and orange oil and combinations thereof.

8. The hair oil product according to claim 1, wherein said first part further comprises between 55-65% castor oil.

9. The hair oil product according to claim 8 wherein said first part further comprises at least one further component selected from the group consisting of: biotin, methylsulfonylmethane (MSM) and saw palmetto and combinations thereof.

10. The hair oil product according to claim 8, wherein said second part comprises two or more vegetable oils selected from the group consisting of: olive oil, grape oil, avocado oil, coconut oil, and macadamia oil and combinations thereof.

11. The hair oil product according to claim 8, wherein said third part comprises two or more aromatic oils selected from the group consisting of: lavender oil, eucalyptus oil, rosemary oil, peppermint oil, lemongrass oil, cedarwood oil, and orange oil and combinations thereof.

12. The hair oil product according to claim 8 wherein said third part further comprises a second vegetable oil selected from the group consisting of: sunflower oil, sesame oil, jojoba oil, and sweet almond oil, safflower oils, walnut oil, olive oil, grapeseed oil, thyme oil, and argan oil and combinations thereof.

13. A method of treating hair by applying a hair oil product according to claim 1 to a person's scalp.

14. A method of making a hair oil product for the conditioning and treatment of hair, the method of making the hair oil product comprising the steps of:
  (a) forming a first part by:
    i. layering castor oil with black tea to form a solution, said solution comprising at least 50% castor oil;
    ii. baking the solution;
    iii. straining the solution;
  (b) forming a second part by
    i. by combining a vegetable oil with at least one of: neem powder, rose petal powder, alma powder; and at least one of: Bhringraj powder, Brahmi powder, and herma powder;
  (c) forming a third part by making a solution by combining an aromatic oil with at least a second vegetable oil, said third part comprising at least 75% vegetable oil;
  (d) combining said second and said third part to form a solution; and
  (e) combining the solution of step d. with said first part, thereby forming a solution for conditioning and treating the hair.

15. The method of claim 8, wherein the vegetable oil of said second part is selected from the group consisting of: olive oil, grape oil, avocado oil, coconut oil, and macadamia oil, and combinations thereof.

16. The method of claim 8, wherein the second vegetable oil said third part is selected from the group consisting of: sunflower oil, sesame oil, jojoba oil, and sweet almond oil, safflower oils, walnut oil, olive oil, grapeseed oil, thyme oil, and argan oil and combinations thereof.

\* \* \* \* \*